(12) United States Patent
Chavarria et al.

(10) Patent No.: US 12,208,015 B2
(45) Date of Patent: Jan. 28, 2025

(54) SYSTEM AND METHOD FOR IMPLANTING A SECONDARY GLENOID PROSTHESIS

(71) Applicant: DEPUY SYNTHES PRODUCTS, INC., Raynham, MA (US)

(72) Inventors: Jason M. Chavarria, Warsaw, IN (US); Kyle E. Lappin, Ft. Wayne, IN (US); Matthew G. Holda, Noblesville, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 954 days.

(21) Appl. No.: 17/235,185

(22) Filed: Apr. 20, 2021

(65) Prior Publication Data
US 2021/0236292 A1    Aug. 5, 2021

Related U.S. Application Data

(60) Continuation of application No. 15/689,111, filed on Aug. 29, 2017, now Pat. No. 10,980,640, which is a continuation of application No. 14/704,607, filed on May 5, 2015, now Pat. No. 9,763,798, which is a division of application No. 13/796,793, filed on Mar. 12, 2013, now Pat. No. 9,044,330.

(51) Int. Cl.
*A61F 2/40* (2006.01)
*A61F 2/46* (2006.01)
*A61F 2/30* (2006.01)

(52) U.S. Cl.
CPC .............. *A61F 2/4081* (2013.01); *A61F 2/40* (2013.01); *A61F 2/4612* (2013.01); *A61F 2002/30484* (2013.01); *A61F 2002/3069* (2013.01); *A61F 2002/30736* (2013.01); *A61F 2/30749* (2013.01); *A61F 2002/4085* (2013.01)

(58) Field of Classification Search
CPC .......... A61F 2/4081; A61F 2/40; A61F 2/4612
See application file for complete search history.

(56) References Cited

U.S. PATENT DOCUMENTS 5,163,964 A    11/1992 Lazzeri et al.
5,593,448 A    1/1997 Dong
(Continued)

FOREIGN PATENT DOCUMENTS

CN    101156810 A    4/2008
CN    102014802 A    4/2011
(Continued)

OTHER PUBLICATIONS

Search Report issued in connection with Chinese Application No. 201410088948.7 by the State Intellectual Property Office of People's Republic China, Jan. 16, 2017, 3 pages.
(Continued)

*Primary Examiner* — Suzette J Gherbi
(74) *Attorney, Agent, or Firm* — Barnes & Thornburg LLP

(57) ABSTRACT

A method of implanting a shoulder prosthesis in a scapula of a patient includes the step of placing a guide over a primary glenoid component previously implanted within the scapula of the patient. The method further includes the steps of removing the primary glenoid component from the scapula and preparing the scapula for implantation of a secondary glenoid component, wherein the removing and preparing steps occur simultaneously.

16 Claims, 8 Drawing Sheets

(56) References Cited

U.S. PATENT DOCUMENTS

| | | | |
|---|---|---|---|
| 6,102,953 A | 8/2000 | Huebner | |
| 6,364,910 B1 | 4/2002 | Shultz et al. | |
| 6,379,386 B1 | 4/2002 | Resch et al. | |
| 6,503,253 B1 | 1/2003 | Fletcher et al. | |
| 7,806,898 B2 | 10/2010 | Justin et al. | |
| 7,867,236 B2 | 1/2011 | Hodorek et al. | |
| 7,892,287 B2 | 2/2011 | Deffenbaugh | |
| 8,231,683 B2 | 7/2012 | Lappin et al. | |
| 8,425,614 B2 | 4/2013 | Winslow et al. | |
| 8,489,076 B2 | 7/2013 | Kim | |
| 8,506,569 B2 | 8/2013 | Keefer et al. | |
| 8,551,177 B2 * | 10/2013 | De Wilde | A61F 2/4081 606/80 |
| 8,556,901 B2 | 10/2013 | Anthony et al. | |
| 8,864,834 B2 | 10/2014 | Boileau et al. | |
| 8,882,845 B2 * | 11/2014 | Wirth | A61F 2/4081 623/19.13 |
| 9,044,330 B2 | 6/2015 | Chavarria et al. | |
| 9,226,830 B2 * | 1/2016 | De Wilde | A61B 17/1778 |
| 9,763,798 B2 | 9/2017 | Chavarria et al. | |
| 10,172,715 B2 * | 1/2019 | De Wilde | A61B 17/1684 |
| 2005/0261775 A1 | 11/2005 | Baum et al. | |
| 2006/0009774 A1 | 1/2006 | Goble et al. | |
| 2006/0074430 A1 | 4/2006 | Deffenbaugh et al. | |
| 2007/0142917 A1 | 6/2007 | Roche et al. | |
| 2008/0183297 A1 | 7/2008 | Boileau et al. | |
| 2010/0023068 A1 | 1/2010 | Bouttens et al. | |
| 2010/0087927 A1 | 4/2010 | Roche et al. | |
| 2010/0161066 A1 | 6/2010 | Iannotti et al. | |
| 2010/0268238 A1 | 10/2010 | Sikora et al. | |
| 2011/0028977 A1 | 2/2011 | Rauscher et al. | |
| 2011/0029088 A1 | 2/2011 | Rauscher et al. | |
| 2011/0137424 A1 * | 6/2011 | Lappin | A61F 2/4081 623/19.11 |
| 2011/0213371 A1 | 9/2011 | Anthony et al. | |
| 2011/0213372 A1 | 9/2011 | Keefer et al. | |
| 2012/0191201 A1 * | 7/2012 | Smits | A61F 2/4014 623/19.11 |
| 2012/0197258 A1 | 8/2012 | Chavarria et al. | |
| 2012/0226283 A1 | 9/2012 | Meridew et al. | |
| 2012/0239156 A1 | 9/2012 | De Wilde et al. | |
| 2012/0253467 A1 | 10/2012 | Frankle | |
| 2013/0197651 A1 | 8/2013 | McDaniel et al. | |
| 2013/0296870 A1 | 11/2013 | Keefer et al. | |
| 2014/0018927 A1 * | 1/2014 | De Wilde | A61F 2/4081 623/19.11 |

FOREIGN PATENT DOCUMENTS

| | | |
|---|---|---|
| CN | 102085124 A | 6/2011 |
| EP | 2777626 A1 | 9/2014 |
| FR | 2652498 A1 | 4/1991 |
| JP | 2000197651 A | 7/2000 |
| JP | 2008183412 A | 8/2008 |
| JP | 2009513285 A | 4/2009 |
| JP | 2011120905 A | 6/2011 |

OTHER PUBLICATIONS

European Search Report, European Patent Application No. 14157143.0, Jun. 2, 2014, 5 pages.

Japanese Office Action with English translation, Japanese Application No. 2014-047351, dated Oct. 31, 2017, 4 pages.

* cited by examiner

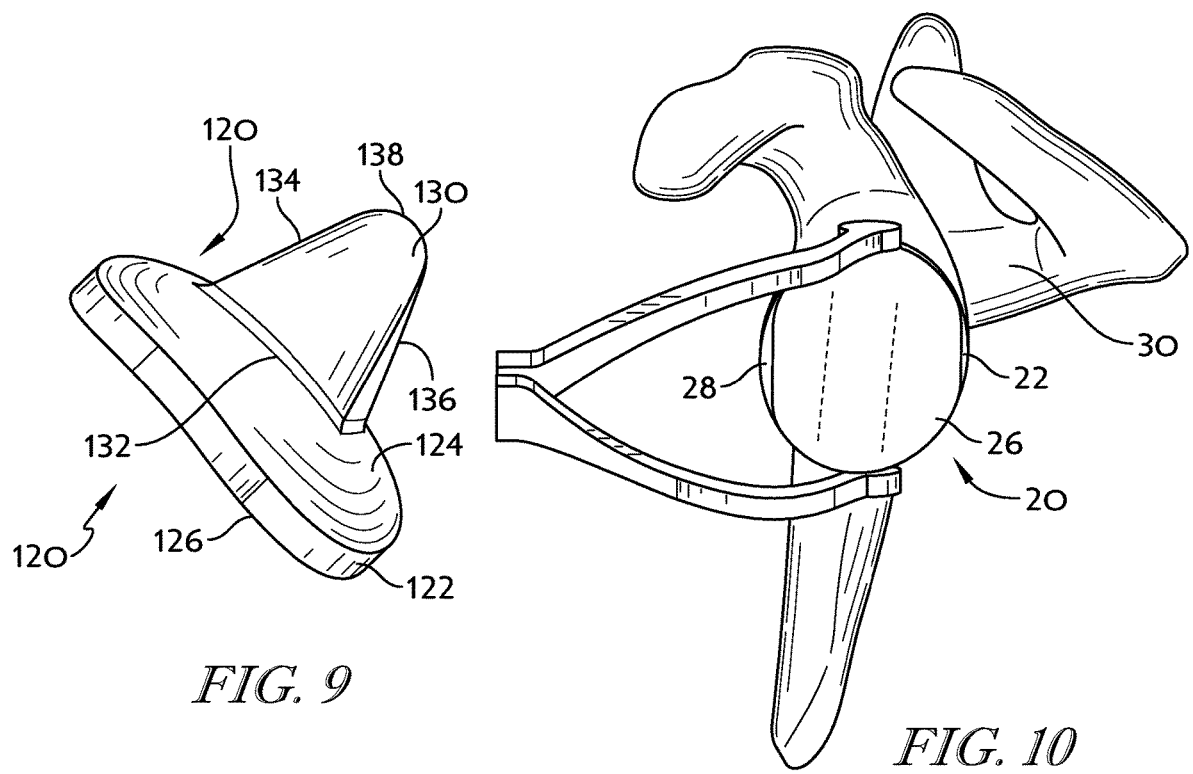
FIG. 9
FIG. 10
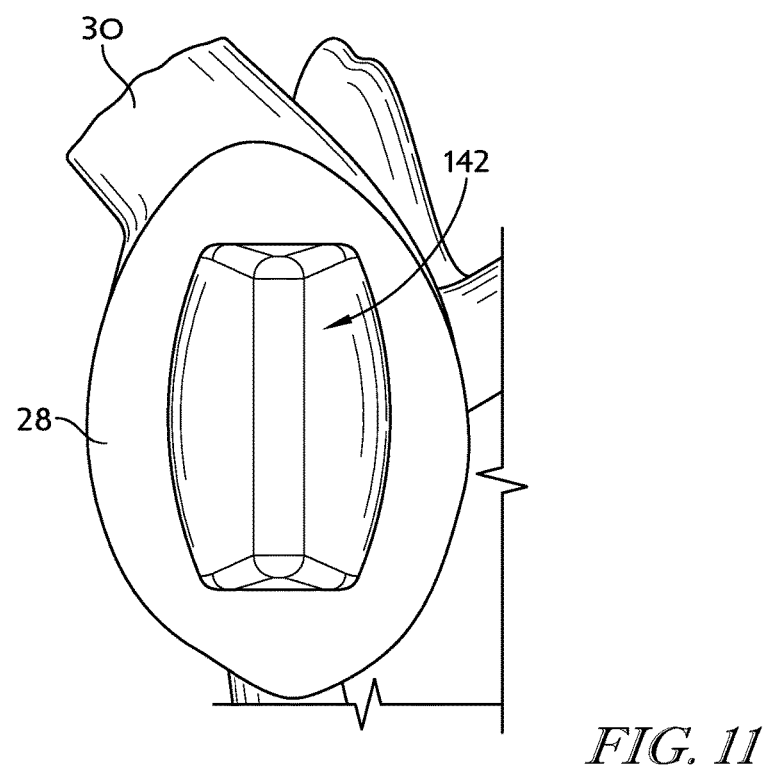
FIG. 11

SYSTEM AND METHOD FOR IMPLANTING A SECONDARY GLENOID PROSTHESIS

This application is a continuation of U.S. patent application Ser. No. 15/689,111, filed Aug. 29, 2017 and now issued as U.S. Pat. No. 10,980,640, which is a continuation of U.S. patent application Ser. No. 14/704,607, filed May 5, 2015 and now issued as U.S. Pat. No. 9,763,798, which is a divisional of U.S. patent application Ser. No. 13/796,793, filed Mar. 12, 2013 and now issued as U.S. Pat. No. 9,044,330. Each of the above-noted applications is incorporated herein by reference.

TECHNICAL FIELD

The present disclosure relates generally to orthopaedic implants, and more particularly to, a system and method for implanting a secondary glenoid prosthesis.

BACKGROUND

During the lifetime of a patient, it may be necessary to perform a total shoulder replacement procedure on the patient as a result of, for example, disease or trauma. In a total shoulder replacement procedure, a humeral prosthesis is used to replace the natural head of the patient's humerus. The humeral prosthesis typically includes an elongated stem component that is implanted into the intramedullary canal of the patient's humerus and a hemispherically-shaped prosthetic head component that is secured to the stem component. In such a total shoulder replacement procedure, the natural glenoid surface of the scapula is resurfaced or otherwise replaced with a glenoid component that provides a bearing surface upon which the prosthetic head component of the humeral prosthesis articulates.

However, in some cases the patient's natural shoulder, including its soft tissue, has degenerated to a severe degree of joint instability and pain. In many such cases, it may be necessary to change the mechanics of the shoulder. Reverse shoulder implants are used to do so. As its name suggests, a reverse shoulder implant reverses the anatomy, or structure, of the healthy shoulder. In particular, a reverse shoulder implant is designed such that the prosthetic head (i.e., the "ball" in the ball-and-socket joint) known as a glenosphere component is secured to the patient's scapula, with the corresponding concave bearing (i.e., the "socket" in the ball-and-socket joint) known as a humeral cup being secured to the patient's humerus. Such a reverse configuration allows the patient's deltoid muscle, which is one of the larger and stronger shoulder muscles, to raise the arm.

SUMMARY

According to one aspect, a method of implanting a shoulder prosthesis in a scapula of a patient includes the step of placing a guide over a primary glenoid component previously implanted within the scapula of the patient. The method further includes the steps of removing the primary glenoid component from the scapula and preparing the scapula for implantation of a secondary glenoid component, wherein the removing and preparing steps occur simultaneously.

The removing step may include the step of utilizing a tool to penetrate the primary glenoid and into the glenoid surface of the scapula. The removing step may further include the step of creating a void in the bone tissue of the scapula that is at least as large as and occupies at least as much space as an anchor extending from the primary glenoid component and which implants the primary glenoid component within the bone tissue of the scapula, thereby eliminating the anchor. Still further, the removing step may include the step of removing unanchored primary glenoid component from the bone tissue of the scapula.

The scapula may be prepared for implantation of the secondary glenoid component by creation of the void in the bone surface of the scapula.

The method may further include the steps of providing a secondary glenoid component comprising an anchor having a geometry that generally conforms to a geometry of the void in the bone tissue of the scapula and implanting the anchor of the secondary glenoid component within the void.

The method may further includes the step of assessing the extent of damage to the shoulder of the patient. If the extent of damage is at a first level, the method may include the step of implanting an anchor of an anatomic secondary glenoid component within the void. Alternatively, if the extent of the damage is at a second level, the method may include the step of implanting an anchor of a reverse secondary glenoid component within the void. The anchor of the anatomic secondary glenoid component and the anchor of the reverse secondary glenoid have geometries that generally conform to a geometry of the void.

According to another aspect, a method of implanting a shoulder prosthesis in a scapula of a patient includes the step of creating a void in the scapula of the patient by penetrating the primary glenoid component, wherein the void encompasses an area within the bone tissue of the scapula occupied by an anchor extending from the primary glenoid component and implanted within the scapula of the patient. The method further includes the steps of removing fragments of the primary glenoid component that are no longer anchored to the bone tissue of the scapula after the step of creating a void and implanting a secondary glenoid component within the void.

The secondary component may include a platform having a lateral surface and a medial surface opposite the lateral surface and adapted to contact the scapula of the patient. The platform may further include at least one anchor extending from the medial surface of the platform, wherein the anchor is adapted to be implanted within the void.

The anchor may be in the form of a peg extending outwardly from a central portion of the medial surface of the platform. Alternatively, the anchor may be in the form of a keel extending outwardly from the medial surface of the platform.

The method may further include the step of assessing the extent of damage to the shoulder of the patient during surgery. If the extent of the damage is at a first level, the method may further include the step of implanting an anchor of an anatomic secondary glenoid component within the void. Alternatively, if the extent of the damage is at a second level, the method may further include the step of implanting an anchor of a reverse secondary glenoid component within the void. The anchor of anatomic secondary glenoid component and the anchor of the reverse secondary glenoid may have geometries that generally conform to a geometry of the void. In addition, the assessing step allows a surgeon to change plans intra-operatively between anatomic and reverse secondary glenoid components.

The step of creating the void may further include the steps of placing a guide over a primary glenoid component previously implanted within the scapula of the patient and removing the primary glenoid component from the scapula. The step of creating the void still further may include the step of preparing the scapula for implantation of a secondary glenoid component, wherein the removing and preparing steps occur simultaneously.

The scapula may be prepared for implantation of the secondary glenoid component by creation of the void in the glenoid surface of the scapula.

The method may further include the steps of providing the secondary glenoid component comprising an anchor having dimensions that conform to dimensions of the void in the glenoid surface of the scapula and implanting the anchor of the secondary glenoid component within the void.

According to yet another aspect, a method of implanting a shoulder prosthesis in a scapula of a patient includes the steps of accessing the bone tissue of the patient's scapula, creating a void within the bone tissue of the patient's scapula, and assessing the extent of damage to the shoulder of the patient. If the extent of the damage is at a first level, the method may further include the step of implanting a first anchor of an anatomic glenoid component within the void. If the extent of the damage is at a second level, the method may further include the step of implanting a second anchor of a reverse glenoid component within the void. The first anchor of the anatomic glenoid component and the second anchor of the reverse secondary glenoid may have geometries that conform generally conform to a geometry of the void.

The method may further include the steps of placing a guide over a primary glenoid component previously implanted within the scapula of the patient and removing the primary glenoid component from the scapula. The method may further include the step of preparing the scapula for implantation of a secondary glenoid component, wherein the removing and preparing steps occur simultaneously.

The anatomic glenoid component and the reverse glenoid component may be part of a platform system. The platform system may include a platform having an anchor extending therefrom and a bearing attachable to the platform and having a bearing surface that forms an articulation surface for articulation of a humeral head, wherein the bearing forms the anatomic glenoid component. The platform system may further include a glenosphere component attachable to the platform and having a surface that articulates upon a bearing surface of a humeral cup.

The method may further include the step of determining intra-operatively whether to implant an anatomic secondary glenoid component or a reverse anatomic glenoid component.

The determining step may be undertaken after implanting the anchor of the platform within the bone tissue of the scapula and, once the determining step is completed, either the bearing or the glenosphere component may be attached to the platform.

In a further aspect, a system for implanting a shoulder prosthesis in a scapula of a patient includes a primary glenoid component including an anchor adapted to be implanted within the scapula of the patient in a primary surgical procedure. The system further includes a secondary glenoid component adapted to be implanted within the scapula of the patient in a secondary surgical procedure. The secondary glenoid component includes a platform having an anchor extending therefrom and a glenosphere component attachable to the platform and having a surface that articulates upon a bearing surface of a humeral cup and which forms a reverse secondary glenoid component. The anchor of the secondary glenoid component includes features similar to features of the anchor of the primary glenoid component.

In an embodiment, the secondary glenoid component is a system that also includes a bearing attachable to the platform and having a bearing surface that forms an articulation surface for articulation of a humeral head, wherein the baring forms an anatomic secondary glenoid component.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which:

FIG. 9 is a perspective view of an illustrative primary glenoid component in the form of a keeled glenoid component for implantation within the bone tissue of a patient's scapula;

FIG. 10 is a perspective view of the primary glenoid component of FIG. 9 implanted within the bone tissue of the patient's scapula and a saw guide positioned atop a concave bearing surface of the primary glenoid component;

FIG. 11 is a perspective view of the glenoid surface of the patient's scapula after a keel of the primary glenoid component has been sawed out, leaving a void in the bone tissue of the patient's scapula, and after a reminder of the primary glenoid component has been removed therefrom;

DETAILED DESCRIPTION OF THE DRAWINGS

Figure 1:
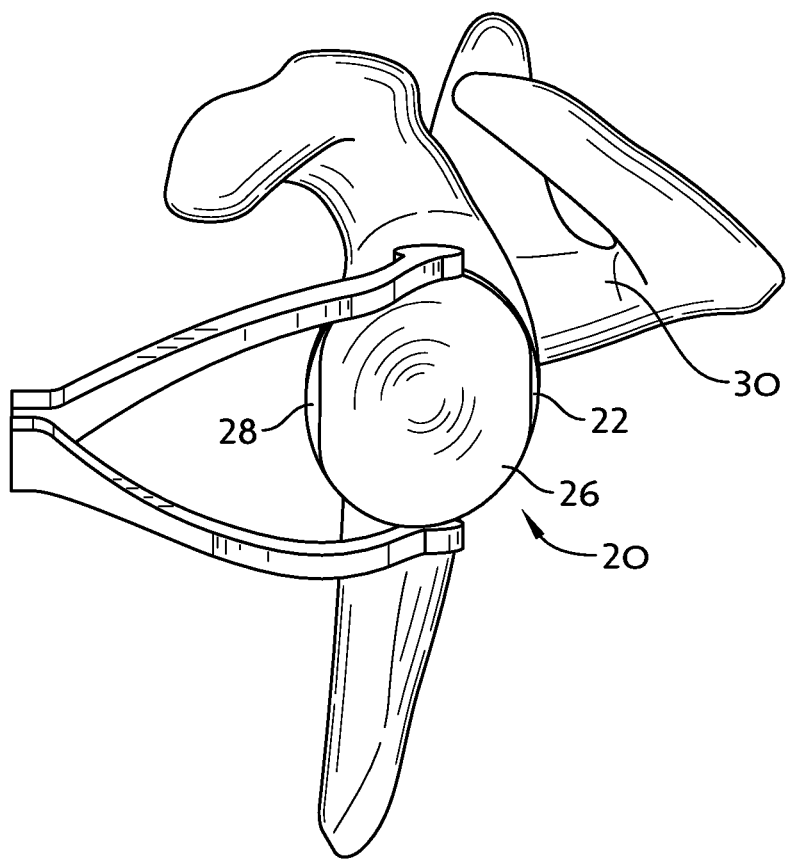
FIG. 1 is a perspective view of a primary glenoid component implanted within bone tissue of a patient's scapula.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 2:
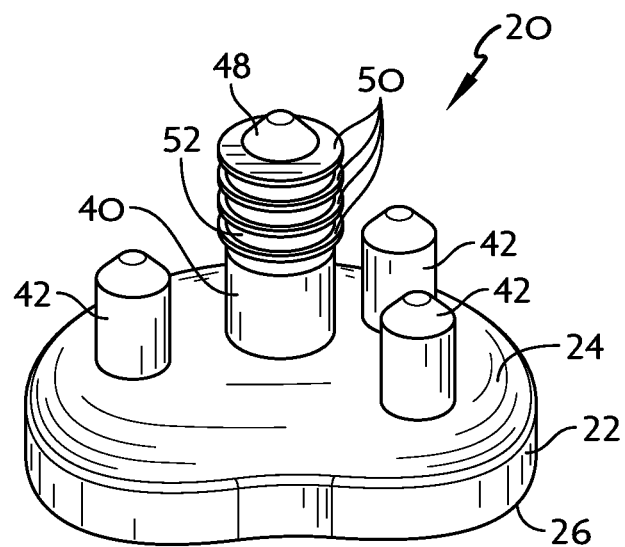
FIG. 2 is a perspective view of an illustrative primary glenoid component in the form of a pegged glenoid component for implantation within the bone tissue of the patient's scapula.

Referring now to the figures, an illustrative primary polymer glenoid component 20 is depicted in FIGS. 1 and 2. The glenoid component 20 includes a body 22 having a first generally convex surface 24 and a second generally concave surface 26 opposite the convex surface 24. The convex surface 24 of the body 22 is configured to abut or otherwise contact a prepared glenoid surface 28 of a patient's scapula 30, as will be discussed in greater detail hereinafter. The concave surface 26 of the body 22 provides a smooth bearing surface upon which a natural or prosthetic humeral head (not shown) articulates.

The glenoid component 20 also includes an anchor peg 40 and a number of stabilizing pegs 42 secured to and extending generally orthogonal to the convex surface 24 of the body 22. As shown in FIGS. 1 and 2, the anchor peg 40 includes a tapered head 48 that functions as a lead-in to facilitate insertion into a hole drilled or otherwise formed in a glenoid surface 28. The anchor peg 40 also includes a plurality of flexible radial fins 50 extending outwardly from a top end 52 of the anchor peg 40. The glenoid component 20 is discussed in greater detail in U.S. Pat. No. 6,699,289, entitled "Augmented Glenoid Component Having an Interrupted Surface and Associated Method for Securing the Augmented Glenoid Component to a Glenoid Surface of a Scapula" and U.S. Pat. No. 6,911,047, entitled "Apparatus and method for securing a cementless glenoid component to a glenoid surface of a scapula", the disclosures of which are incorporated herein in their entireties.

The glenoid component 20 may be constructed of a polymeric material, for example, a polyethylene. One example of a suitable polyethylene is ultrahigh molecular weight polyethylene (UHMWPE).

During a primary surgical procedure, the glenoid surface 28 of the patient's scapula 30 is prepared and bores are drilled into the prepared glenoid surface 28 of the patient's scapula 30. The primary glenoid component 20 is thereafter implanted within the bone tissue of the scapula 30 with the convex surface 24 of the body 22 abutting or otherwise contacting the prepared glenoid surface 28, with the anchor peg 40 and stabilizing pegs 42 extending into the bores. While the radial fins 50 aid in retaining the anchor peg 40 within a respective bore, bone cement may alternatively or additionally be used. The installed glenoid component 20 is shown in FIG. 1. The glenoid component 20 may alternatively be implanted in any suitable manner.

Figure 3:
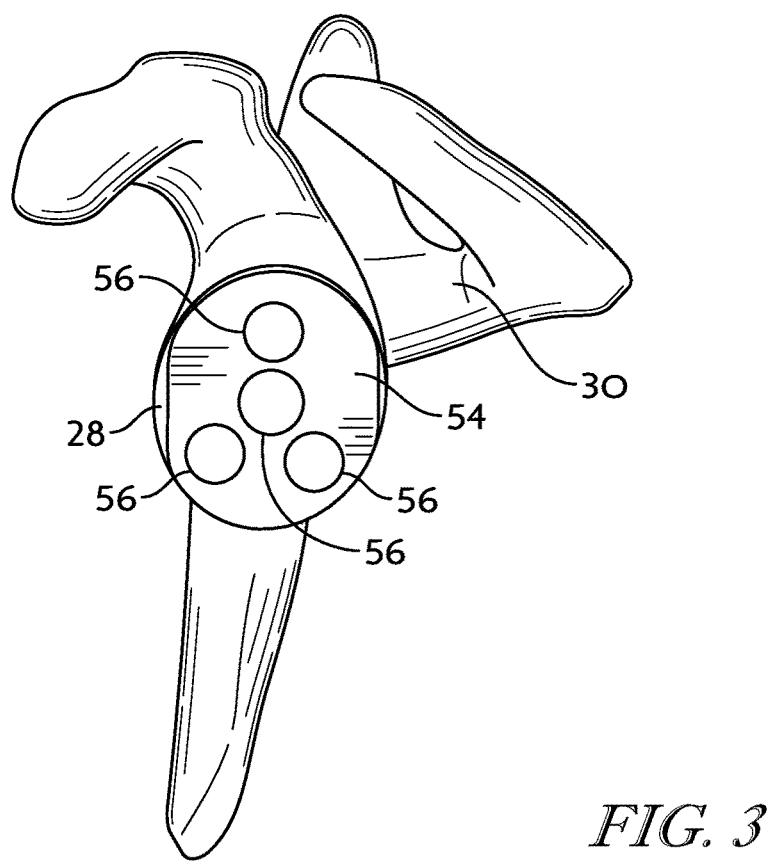
FIG. 3 is a perspective view similar to the view of FIG. 1 with a drill guide positioned atop a concave bearing surface of the primary glenoid component of FIGS. 1 and 2.
Figure 4:
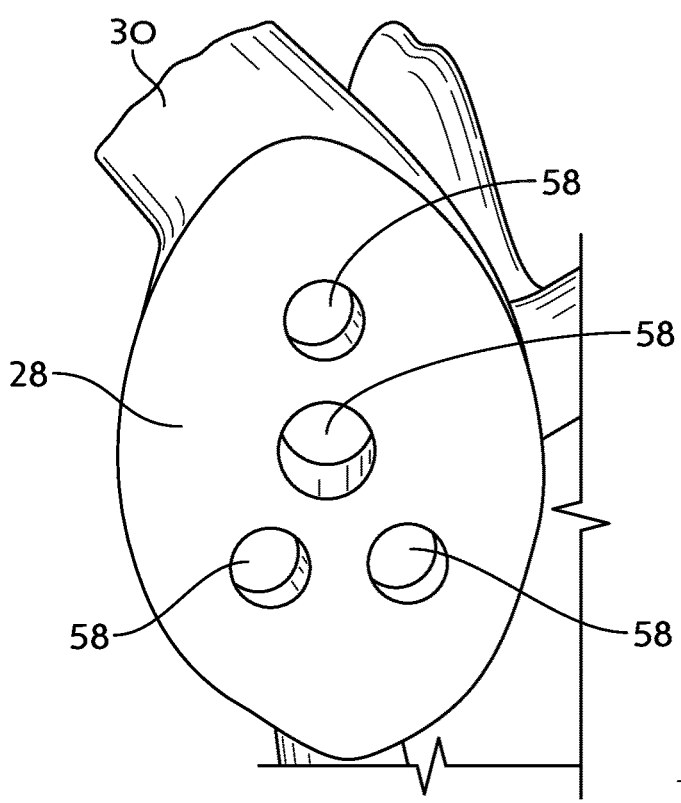
FIG. 4 is an enlarged perspective view of the glenoid surface of the patient's scapula after pegs of the primary glenoid component have been drilled out, leaving bores in the bone tissue of the patient's scapula, and after a remainder of the primary glenoid component has been removed therefrom.

During a revision surgical procedure of the present disclosure, a drill guide 54 is placed over the concave surface 26 of the glenoid component 20, as seen in FIG. 3. Holes 56 in the drill guide 54 are positioned in alignment with the anchor peg 40 and the stabilizing pegs 42. A drill is thereafter aligned with the holes 56 in the drill guide 54 to drill out the anchor peg 40 and the stabilizing pegs 42. In this manner, the anchor peg 40 and the stabilizing pegs 42 are removed by the drill, leaving the body 22 of the glenoid component 20 and bores 58 where the anchor peg 40 and stabilizing pegs 42 were implanted during the primary surgical procedure. The body 22 of the glenoid component 20 may be removed, leaving the bores 58 in the bone tissue of the patient's scapula 30, as seen in FIG. 4.

Figure 5:
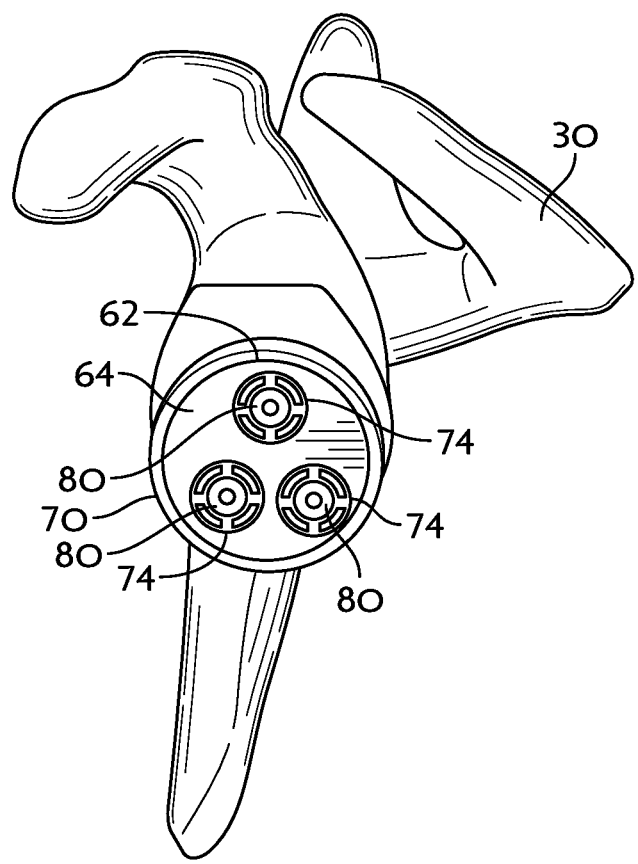
FIG. 5 is a perspective view of a metaglene component of a secondary glenoid component implanted within the bone tissue of the patient's scapula.
Figure 6:
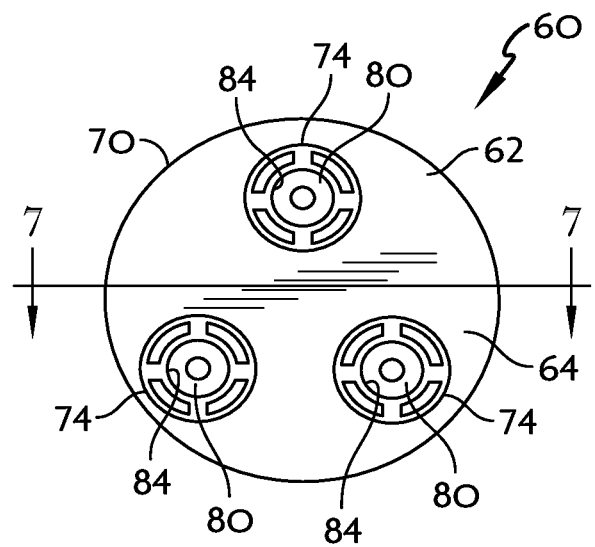
FIG. 6 is a top elevational view of the metaglene component of FIG. 5.
Figure 7:
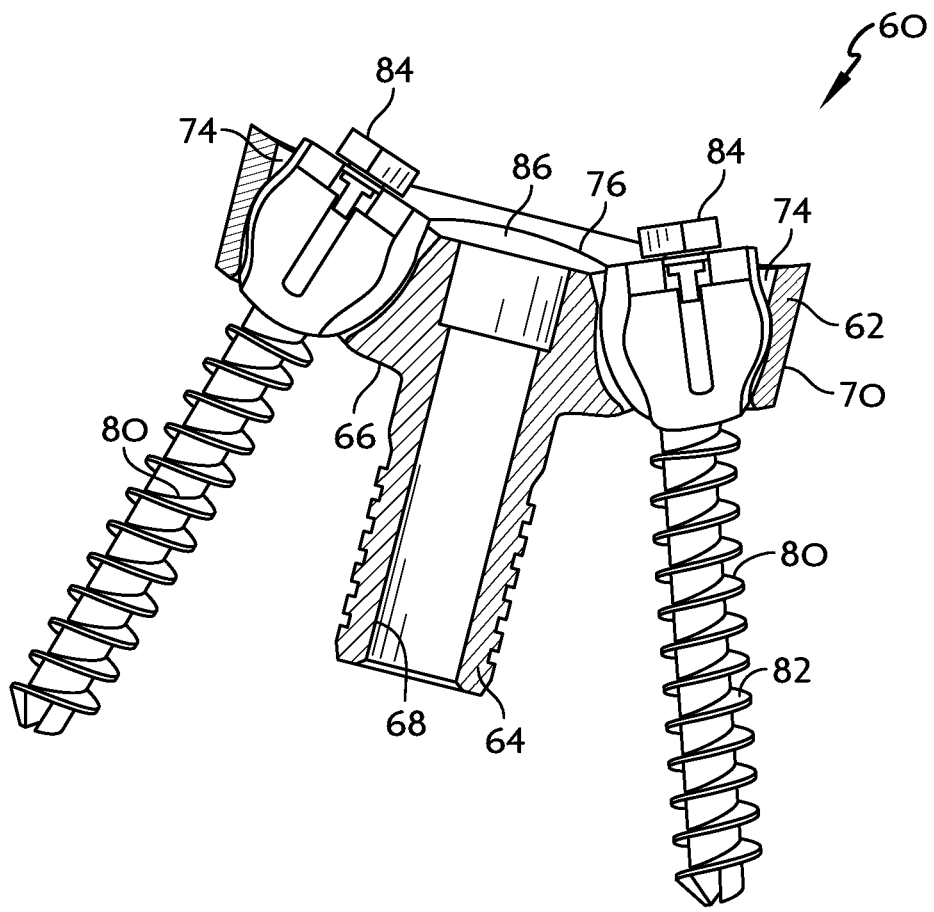
FIG. 7 is a cross-sectional view taken generally along the lines 7-7 of FIG. 6, illustrating a central bore extending through a stem of the metaglene component and compression screws extending through a platform of the metaglene component.

A secondary glenoid component in the form of a metaglene component 60, as seen in FIGS. 6 and 7, may be implanted within the bone tissue of the patient's scapula, as seen in FIG. 5, during a revision surgical procedure. The metaglene component 60 includes a platform 62 having a stem 64 extending outwardly from its medial surface 66. The stem 64 of the metaglene component 60 is configured to be implanted into the surgically-prepared bone tissue of the patient's scapula 30. The stem 64 has a bore 68 formed therein. The bore 68 extends through the entire length of the stem 64, although it could be embodied as a blind bore. An outer annular surface 70 of the platform 62 is tapered inwardly between a lateral surface 76 and the medial surface 66 of the platform 62, the function of which will be described in detail below.

As depicted in FIGS. 6 and 7, a number of screw holes 74 extend through the platform 62 of the metaglene component 60. In an illustrative embodiment, the platform 62 includes three screw holes 74 extending through the platform 62, which are adapted to be aligned with the bores 58 in the glenoid surface 28. Each of the screw holes 74 opens into the medial surface 66 of the platform 62, with its other end opening into the lateral surface 76 of the platform 62. Each of the screw holes 74 may be counterbored to accommodate screw heads of compression screws 80 used to secure the metaglene component 60 to the bone tissue of the patient's scapula 30. As such, upper ends of the screw holes 74 would have a larger diameter than lower ends of the screw holes 74. The bore 68 may also be capable of accepting a compression screw 80 in alignment with a bore 58 that was previously occupied by the anchor peg 40 of the primary glenoid component 20.

In the illustrative embodiment of FIGS. 6 and 7, each of the screw holes 74 is spaced outwardly from a center of the platform 62 of the metaglene component 60 at a position between the bore 68 and its tapered outer annular surface 70. Each of the screw holes 74 is depicted as being positioned about 120 degrees from an adjacent screw hole 74, but the screw holes 74 may be positioned in any location that corresponds to the placement of the stabilizing pegs 42 of the primary glenoid component 20. Still optionally, if the primary glenoid component 20 does not include stabilizing pegs 42, the metaglene component 60 need not include screw holes 74.

As seen in FIGS. 5-8, the compression screws 80 may be positioned in some or all of the screw holes 74 and/or the bore 68 to secure the metaglene component 60 to the bone tissue of the patient's scapula 30. Each of the screws 80 includes a threaded shank 82 having a screw head 84 on an end thereof. A diameter of the threaded shank 82 is smaller than a diameter of the lower end of the counterbored screw holes 74 of the metaglene component 60 so that the threaded shank 82 may pass through the entire length of the screw holes 74. The screw head 84, on the other hand, has a diameter smaller than the upper end of the counterbored screw holes 74, but larger than the lower end of the counterbored screw holes 74. As such, the screw heads 84 of the compression screws 80 are contained in the upper end of the counterbored screw holes 74 when installed in the metaglene component 60.

The metaglene component 60 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic metaglene component 60 may also be coated with a surface treatment, such as hydroxyapatite, to enhance biocompatibility. Moreover, the surfaces of the metaglene component 60 that engage the natural bone, such as the medial surface 66 of platform 62 and an outer surface of the stem 64 may be textured to facilitate securing the component to the bone. Such surfaces may also be porous coated to promote bone ingrowth for permanent fixation.

Like the metaglene component 60, the compression screws 80 may be constructed with an implant-grade biocompatible metal, although other materials may also be used. Examples of such materials include cobalt, including cobalt alloys such as a cobalt chrome alloy, titanium, including titanium alloys such as a Ti6Al4V alloy, and stainless steel.

As seen in FIG. 5, the metaglene component 60 is implanted within the bone tissue of the scapula 30 by positioning the stem 64 of the metaglene component 60 within the bore 58 previously occupied by the anchor peg 40 of the primary glenoid component 20, and thereafter fixing the metaglene component 60 in place by inserting one or more compression screws 80 through the screw holes 74 and driving them into the bone tissue of the patient's scapula 30. In particular, the screws 80 may be inserted into the screw holes 74 and thereafter implanted within the bores 58 formed in the scapula 30, which were previously occupied by the stabilizing pegs 42 of the primary glenoid component 20.

Figure 12:
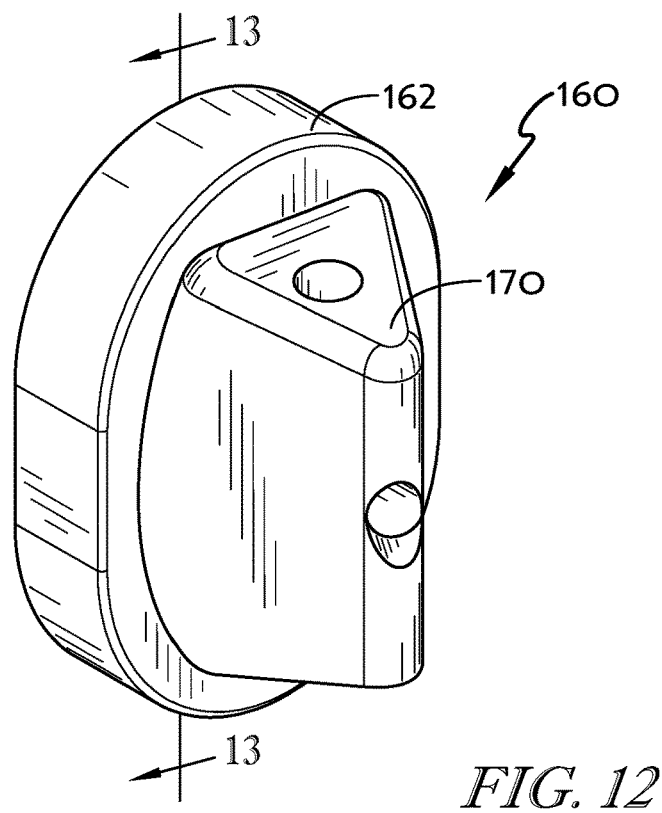
FIG. 12 is a perspective view of a vaulted component of a secondary glenoid component for implantation within the void of FIG. 11.

Depending on the extent of damage to the shoulder, for example, the cuff, bone tissue, etc., a reverse shoulder orthopaedic implant may be necessary. The reverse shoulder orthopaedic implant includes the metaglene component 60 and a glenosphere component 190, as seen in FIG. 12. The glenosphere component 190 is secured to the glenoid surface 28 of the patient's scapula 30 by the metaglene component 60, which is implanted in the bone tissue of the scapula 30. The glenosphere component 190 articulates on a bearing surface of a humeral cup of a humeral prosthesis (not shown). The glenosphere component 190 may be similar to that discussed below in relation to FIG. 12.

In other instances, during a revision surgical procedure, the damage to the shoulder, for example, the cuff, bone tissue, etc., may not require a reverse shoulder orthopaedic implant. As such, an anatomic bearing similar to the anatomic bearing 220 depicted in FIG. 14, may be secured to the glenoid surface 28 of the patient's scapula 30 by the metaglene component 60, which is implanted in the bone tissue of the scapula 30. The anatomic bearing 220 provides a smooth bearing surface upon which a natural or prosthetic humeral head (not shown) articulates. The anatomic bearing 220 may be similar to that discussed below in relation to FIG. 14, or may be any other suitable anatomic bearing. An anatomic bearing for use with the metaglene component may be may be constructed with a polymeric material, for example, a polyethylene. One example of a suitable polyethylene is ultrahigh molecular weight polyethylene (UHMWPE).

Unlike the glenosphere component 190 and the anatomic bearing 220 that may be provided in various sizes to provide the flexibility necessary to conform to varying anatomies from patient to patient, in an illustrative embodiment, the metaglene component 60 may be provided in a single, "universal" size that accommodates glenosphere components of various sizes. For example, a metaglene component 60 may be provided in a single size to accommodate both a 38 mm glenosphere component 190 and a 42 mm glenosphere component 190.

Referring to FIGS. 9 and 10, a primary polymer keeled glenoid component 120 is depicted. The keeled glenoid component 120 includes a body 122 having a first generally convex surface 124 and a second generally concave surface 126 opposite the convex surface 124. The convex surface 124 of the body 122 is configured to abut or otherwise contact a prepared glenoid surface 28 of a patient's scapula 30. The concave surface 126 of the body 122 provides a smooth bearing surface upon which a natural or prosthetic humeral head (not shown) articulates.

The keeled glenoid component 120 further includes an anchor or keel 130 extending from the convex surface 124. The keel 130 may have a shape that is generally triangular with a base 132 integrally connected to the convex surface 124 and angled sides 134, 136 extending from ends of the base 132 and terminating in a rounded end 138. A width of the keel 130 at the base 132 is greater than a width of the keel 130 at the rounded end 138. While the keel 130 is depicted as having a particular shape, the principles of the present disclosure may be applied to a keel 130 having any suitable shape. While the keel 130 is disclosed as being integral with the convex surface 124, the keel 130 may optionally be a separate component that is secured to the convex surface 124.

The body 122 and the keel 130 may be constructed with a polymeric material, for example, a polyethylene. One example of a suitable polyethylene is ultrahigh molecular weight polyethylene (UHMWPE).

During a primary surgical procedure, the glenoid surface 28 of the patient's scapula 30 is prepared and bone shaping tools, such as reamers, saws, drills, burrs, rasps, and the like, are used to shape the glenoid surface 28 to form a cavity that is complementary to the keel 130 of the keeled glenoid component 120. The keeled glenoid component 120 may then be implanted within the cavity using bone cement or the like. The implanted keeled glenoid component 120 is shown in FIG. 10.

During a revision surgical procedure of the present disclosure, a guide having saw slots is positioned over the concave surface 126 of the keeled glenoid component 120, as seen in FIG. 10. A micro saw blade or other appropriate tool may thereafter be positioned within the saw slots, wherein the saw removes a portion of the body 122 of the keeled glenoid component 120 and the keel 130 by boring through the keeled glenoid component 120 and the bone tissue of the patient's scapula 30. Only non-affixed portions of the body 122 remain, which can be removed, thereby leaving a central void 142 within the glenoid surface 28 of the scapula 30, as seen in FIG. 11.

Figure 13:
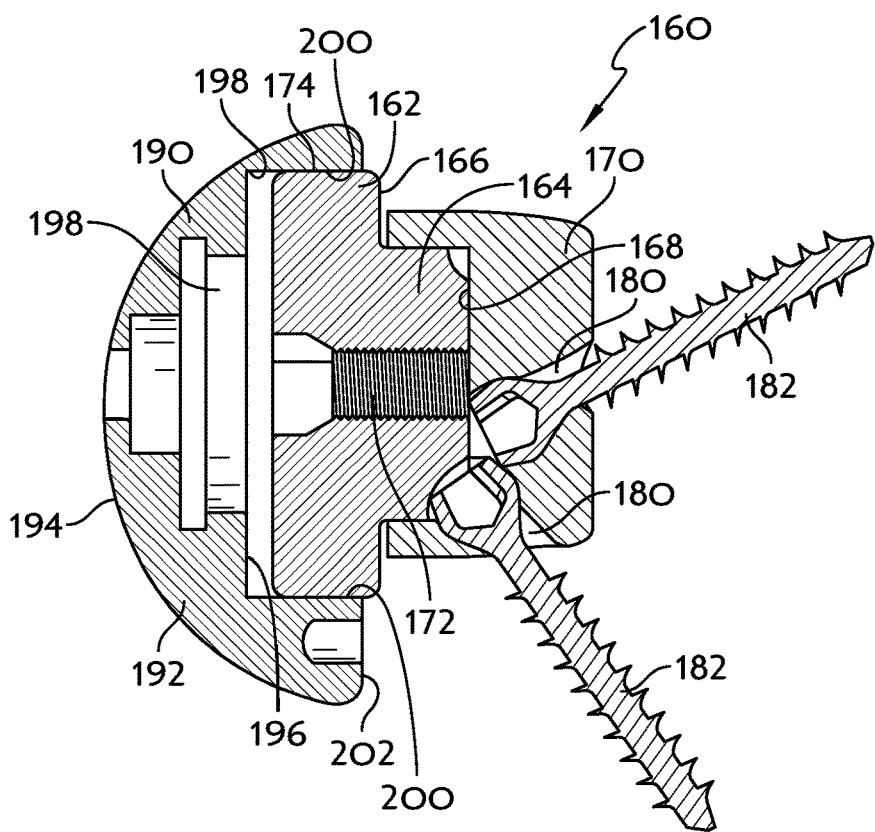
FIG. 13 is a cross-sectional view taken generally along the lines 13-13 of FIG. 12 and illustrating a glenosphere component secured to the vaulted component of FIG. 12.

A vaulted component 160, as seen in FIGS. 12 and 13 may be implanted within the bone tissue of the patient's scapula 30 during a revision surgical procedure. The vaulted component 160 includes a platform 162 having a stem 164 extending outwardly from its medial surface 166. The stem 164 of the vaulted component 160 is configured to be secured within a cavity 168 in a vaulted baseplate 170, which is configured to be implanted within the surgically-prepared bone tissue of the patient's scapula 30. The stem 164 has a threaded bore 172 formed therein. An outer annular surface 174 of the platform 162 is tapered, the function of which will be described in detail below. While the metalgene component 160 and the vaulted baseplate 170 are shown as being separate components, the platform 162 and the vaulted baseplate 170 may be formed integrally as a single piece.

The vaulted baseplate 170 has a geometry that conforms to the central void 142 formed within the glenoid surface 28 of the scapula 30 during preparation of the glenoid surface 28. As depicted in FIGS. 12 and 13, a number of screw holes 180 extend through the vaulted baseplate 170. Each of the screw holes opens into the cavity 168 in the vaulted baseplate 170 and may be counterbored to accommodate screw heads of compression screws 182 used to secure the vaulted component 160 to the bone tissue of the patient's scapula 30. As such, upper ends of the screw holes 180 would have a larger diameter than lower ends of the screw holes 180. The screw holes 180 and screws 182 are similar to the screw holes 74 and screws 80 of FIGS. 5-7.

The platform 162 and the vaulted baseplate 170 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic vaulted component 160 may also be coated with a surface treatment, such as hydroxyapatite, to enhance biocompatibility. Moreover, the surfaces of the vaulted component 160 that engage the natural bone, such as the medial surface 166 of platform 162 and the vaulted baseplate 170 may be textured to facilitate securing the component to the bone. Such surfaces may also be porous coated to promote bone ingrowth for permanent fixation.

A glenosphere component 190 may be secured to the platform 162 of the vaulted component 160 in the case when a reverse shoulder orthopaedic implant is necessary, as discussed above. The glenosphere component 190 includes a body 192 having a curved lateral surface 194. The curved lateral surface 194 of the body 192 provides a smooth bearing surface upon which a bearing surface of a humeral cup (not shown) articulates. The lateral bearing surface 194 may be hemi-ellipsoidal in shape. That is, the lateral bearing surface 194 defines the general shape of ellipsoid sliced in half along its longitudinal plane.

The glenosphere component 190 also includes a substantially flat medial surface 196 opposite its lateral bearing surface 194. The medial surface 196 has a tapered bore 198 formed therein. Tapered sidewalls 200 defining the bore 198 extend laterally away from the medial surface 196 to a bottom wall 202. The tapered outer annular surface 174 of the platform 162 of the vaulted component 160 may be inserted into the tapered bore 198 to engage the sidewalls 200, thereby taper locking the glenosphere component 190 to the vaulted component 160.

The same or a similar glenosphere component 190 may similarly be secured to the platform 62 of the metaglene component 60 of FIGS. 5-7. As noted above, the metaglene component 60 includes a tapered outer annular surface 70 that forms a taper locking with the tapered bore 198 in the same manner as the tapered outer annular surface 174 of FIG. 13.

Figure 14:
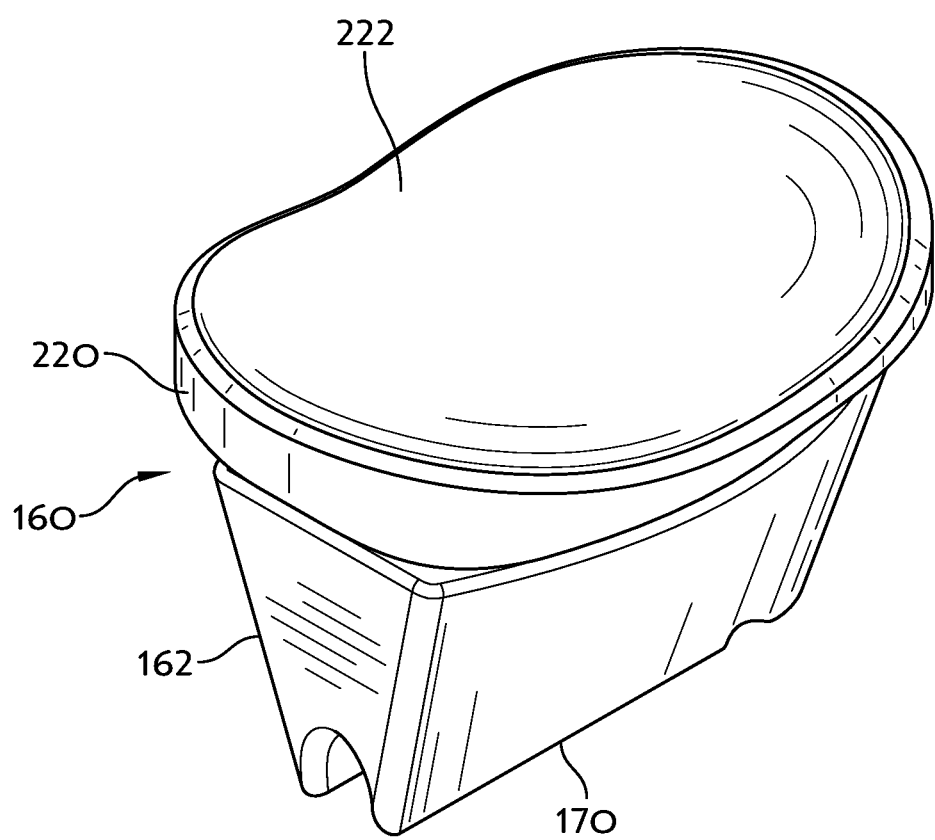
FIG. 14 is a secondary glenoid component having an anatomic bearing secured to the vaulted component.

Referring to FIG. 14, an anatomic bearing 220 may be secured to the platform 162 of the vaulted component 160 in the case when a reverse shoulder orthopaedic implant is not necessary. Similar to the glenosphere component 190, the anatomic bearing 220 generally includes a tapered bore in a medial surface thereof, wherein tapered sidewalls defining the bore engage the tapered outer annular surface 174 of the platform 162 of the vaulted component 160, thereby taper locking the glenosphere anatomic bearing 220 to the vaulted component 160. The anatomic bearing 220 further includes a bearing surface 220 upon which the natural or prosthetic humeral head articulates.

While a particular metaglene component 60, a particular vaulted component 160, a particular glenosphere component 190, and a particular anatomic bearing 220 are depicted, the principles of the present disclosure may be utilized in conjunction with any suitable metaglene components, vaulted components, glenosphere components, and/or anatomic bearings. Similarly, the principles of the present disclosure may be utilized in conjunction with any suitable primary and/or secondary glenoid components.

Typically, revision of a glenoid implant involves both surgical steps related to removal of the primary component and preparation of the bone tissue for implantation of the secondary component. The methods disclosed herein provide a system in which removal of a primary glenoid component simultaneously prepares the glenoid surface and the bone tissue of the patient's scapula for re-implantation of a secondary glenoid component. The simultaneous removal and preparation may reduce the time necessary to perform the surgical procedure and reduce the number of instruments necessary for the surgical procedure. In addition, the simultaneous removal and preparation may reduce bone loss because the same voids (e.g., holes or cavities) for a revision procedure, rather than creating new voids.

The methods, as disclosed in detail above, may generally include the steps of positioning a tool guide atop an implanted primary glenoid component and penetrating the primary glenoid component with a tool. The tool guide provides the surgeon with a guide for the tool such that the tool penetrates and bores through the primary glenoid component and the glenoid surface 28 of the scapula 30 to remove portions of the primary glenoid component that are implanted within the bone tissue of the scapula 30. As such, once the surgeon has finished, the portions of the primary glenoid component that were implanted within the bone tissue of the scapula 30 have been removed and a remainder of the primary glenoid component, which is unattached, may be removed, thereby leaving a void within the glenoid surface 28 of the scapula 30. When a void is referenced with respect to removing the primary glenoid component, it should be understood that the void may be formed by any suitable tool, such as for example, a saw or a drill, and may have any geometry, shape, and/or dimension, for example, a cylindrical hole or any other shape that conforms to a geometry, shape, and/or dimension of an anchor within the secondary glenoid component.

The method further includes the step of implanting a secondary glenoid component within the void. During the surgical procedure, a platform system is provided such that the surgeon may determine intra-operatively whether to implant an anatomic secondary glenoid component or a reverse secondary glenoid component regardless of the surgeon's plan prior to the surgical procedure.

After the primary glenoid component is removed, the surgeon may perform trialing to determine whether an anatomic or reverse secondary glenoid component is necessary. The surgeon may additionally or alternatively make this decision based on the extent of damage to the shoulder (e.g., the cuff). For example, if the extent of damage of the shoulder is minimal, the surgeon may decide intra-operatively to implant an anatomic secondary glenoid component. Conversely, if the extent of damage of the shoulder is greater, the surgeon may decide intra-operatively to implant a reverse secondary glenoid component.

Figure 8:
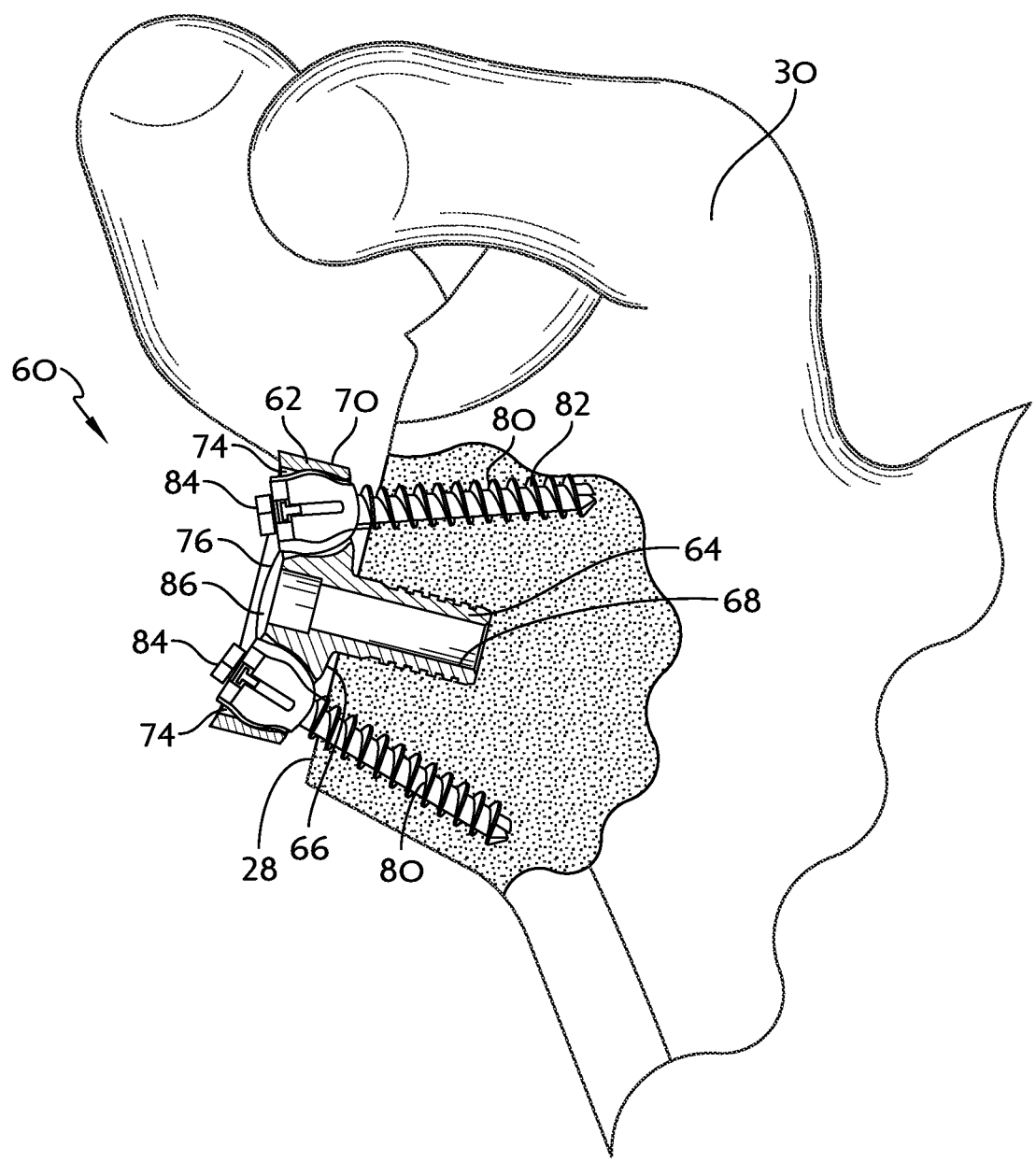
FIG. 8 is a partial cross-sectional view similar to the view of FIG. 7, depicting the metaglene component implanted within the bone tissue of the patient's scapula.

As noted above, a platform system is provided that allows a surgeon to determine intra-operatively between implantation of an anatomic glenoid and a reverse glenoid. In particular, the anatomic and reverse secondary glenoid components may include a single platform including a platform with an anchor that generally conforms in size, shape, and/or dimension to a size, shape, and/or dimension of the void remaining after removal of the primary glenoid component. Further, the anchor may be similar in geometry, shape, and/or dimension to the anchor of the primary glenoid component. As shown in FIGS. 7 and 8, placement of the stem 64 of the metaglene component 60 uses the same antatomic landmarks and instrumentation regardless of whether an anatomic or reverse prosthesis is used. As noted above, this provides a common surgical approach, a more efficient surgical process, reduces the length of the surgical procedure, and reduces the number of necessary instruments in the operating room (and the chances of a missing instrument). This common surgical approach provides the surgeon with more flexibility in his/her surgical approach.

While particular primary and secondary glenoid components are depicted, the principles of the present disclosure may be utilized in conjunction with any primary and/or secondary glenoid components. Exemplary secondary glenoid components for use with the principles of the present disclosure are disclosed in, for example, Lappin et al. U.S. Pat. No. 8,231,683, entitled "Shoulder Prosthesis Assembly Having Glenoid Rim Replacement Structure" and De Wilde et al. U.S. Publication No. 2012/0239156, entitled "Revision Glenoid Device and Method." The disclosures of such documents are incorporated by reference herein in their entireties.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A kit for an orthopaedic shoulder prosthesis, the kit comprising:
a vaulted component, comprising:
a wedge-shaped vaulted baseplate sized and shaped to be received into a surgically-prepared wedge-shaped void in a scapula of a patient, the vaulted baseplate having (i) a planar lateral end having a cavity formed therein, (ii) rounded medial end which is narrower than the planar lateral end of the vaulted baseplate in the anterior/posterior direction, and (iii) a pair of convex sidewalls walls extending between the planar lateral end of the vaulted baseplate and the rounded medial end of the vaulted baseplate, and
a platform having (i) a tapered outer annular surface, and (ii) a stem having an outer surface that engages an inner surface of the vaulted baseplate when the stem is positioned in the cavity of the vaulted baseplate
a fastener configured to secure the vaulted baseplate to the scapula of the patient, and
a glenosphere component having a tapered inner annular surface configured to engage the tapered outer annular surface of the platform, the glenosphere component having a surface that articulates upon a bearing surface of a humeral cup and which forms a reverse glenoid component.

2. The kit of claim 1, wherein:
the vaulted baseplate further includes a pair of planar end walls, and
each of the pair of planar end wall extends between the convex outer sidewalls.

3. The kit of claim 2, wherein:
the vaulted baseplate further includes a bore that extends through a first planar end wall of the pair of planar end walls and opens into the cavity, and
the bore is sized to receive the fastener to secure the vaulted baseplate to the scapula of the patient.

4. The kit of claim 3, wherein the first planar end wall is an inferior planar end wall.

5. The kit of claim 1, wherein:
the vaulted baseplate further includes a bore that extends through its rounded medial end and opens into the cavity,
the bore is sized to receive the fastener to secure the anchor to the scapula of the patient.

6. The kit of claim 1, wherein the vaulted baseplate has a porous outer surface.

7. The kit of claim 1, wherein the platform and the vaulted baseplate are formed from a biocompatible metal.

8. The kit of claim 7, wherein the platform and the vaulted baseplate are formed from at least one of cobalt, a cobalt alloy, titanium, a titanium alloy, and stainless steel.

9. A kit for an orthopaedic shoulder prosthesis, the kit comprising:
a vaulted component, comprising:
a wedge-shaped vaulted baseplate sized and shaped to be received into a surgically-prepared wedge-shaped void in a scapula of a patient, the vaulted baseplate having (i) a planar lateral end having a cavity formed therein, (ii) rounded medial end which is narrower than the planar lateral end of the vaulted baseplate in the anterior/posterior direction, (iii) a pair of convex sidewalls walls extending between the planar lateral end of the vaulted baseplate and the rounded medial end of the vaulted baseplate, and (iv) a pair of bores opening into the cavity, and
a platform having (i) a tapered outer annular surface, and (ii) a stem having an outer surface that engages an inner surface of the vaulted baseplate when the stem is positioned in the cavity of the vaulted baseplate
a pair of fasteners configured to secure the vaulted baseplate to the scapula of the patient, and a glenosphere component having a tapered inner annular surface configured to engage the tapered outer annular surface of the platform, the glenosphere component having a surface that articulates upon a bearing surface of a humeral cup and which forms a reverse glenoid component.

10. The kit of claim 9, wherein:
the vaulted baseplate further includes a pair of planar end walls, and
each of the pair of planar end wall extends between the convex outer sidewalls.

11. The kit of claim 10, wherein:
one of the pair of bores of the vaulted baseplate extends through a first planar end wall of the pair of planar end walls and opens into the cavity, and
the bore that extends through the first planar end wall is sized to receive one of the pair of fasteners to secure the vaulted baseplate to the scapula of the patient.

12. The kit of claim 11, wherein the first planar end wall is an inferior planar end wall.

13. The kit of claim 9, wherein:
one of the bores of the vaulted baseplate extends through its rounded medial end and opens into the cavity, and
the bore that extends through the rounded medial end is sized to receive one of the pair of fasteners to secure the anchor to the scapula of the patient.

14. The kit of claim 9, wherein the vaulted baseplate has a porous outer surface.

15. The kit of claim 9, wherein the platform and the vaulted baseplate are formed from a biocompatible metal.

16. The kit of claim 15, wherein the platform and the vaulted baseplate are formed from at least one of cobalt, a cobalt alloy, titanium, a titanium alloy, and stainless steel.

* * * * *